(12) United States Patent
Hefetz et al.

(10) Patent No.: US 6,369,391 B1
(45) Date of Patent: Apr. 9, 2002

(54) LIGHT OUTPUT OPTIMIZATION (75) Inventors: Yaron Hefetz, Herzelia; Naor Wainer, Zichron-Yaakov; Amir Pansky, Haifa, all of (IL)

(73) Assignee: Elgems Ltd., Tirat-Hagarmec (IL)

( * ) Notice: Subject to any disclaimer, the term of this patent is extended or adjusted under 35 U.S.C. 154(b) by 0 days.

(21) Appl. No.: 09/660,440

(22) Filed: Sep. 12, 2000

Related U.S. Application Data (63) Continuation of application No. PCT/IL99/00225, filed on May 2, 1999.

(51) Int. Cl.$^7$ .............................................. G01T 1/202
(52) U.S. Cl. ...................................................... 250/368
(58) Field of Search ........................................ 250/368

(56) References Cited

U.S. PATENT DOCUMENTS

| | | | |
|---|---|---|---|
| 3,930,160 A | * 12/1975 | Swineheart | 250/361 R |
| 3,970,852 A | * 7/1976 | Richey et al. | 250/363.02 |
| 5,047,642 A | * 9/1991 | Pleyber et al. | 250/368 |
| 5,382,798 A | 1/1995 | Mouyen | |
| 5,430,298 A | * 7/1995 | Possin et al. | 250/370.11 |
| 5,552,606 A | 9/1996 | Jones et al. | |
| 5,616,924 A | 4/1997 | Petrillo | |
| 5,763,887 A | 6/1998 | Murphy | |
| 5,786,599 A | * 7/1998 | Rogers et al. | 250/483.1 |
| 5,861,628 A | * 1/1999 | Genna et al. | 250/368 |

FOREIGN PATENT DOCUMENTS

| | | | |
|---|---|---|---|
| EP | 0 221 503 | 5/1987 | |
| EP | 0 378 896 | 7/1990 | |
| EP | 0 534 683 | 3/1993 | |
| GB | 1 529 215 | 9/1975 | |
| JP | 58-21580 A | * 2/1983 | 250/368 |
| SU | 1612764 A1 | * 3/1993 | 250/368 |
| WO | WO 92/13492 | 8/1992 | |

OTHER PUBLICATIONS

Karp, J. S. et al.; "Performance of a Position–Sensitive Scintillation Detector"; Phys. Med. Biol.; vol. 30; No. 7; 1985; pp. 643–655.

* cited by examiner

*Primary Examiner*—Constantine Hannaher
(74) *Attorney, Agent, or Firm*—Fenster & Company Patent Attorneys, Ltd.

(57) ABSTRACT

A scintillator, having two faces, for use in medical diagnostic imaging devices, said devices including a plurality of light sensors for converting light generated in said scintillators to electrical signals, processors for converting the electrical signals to images and a monitor for displaying the images, said scintillator including a two dimensional distribution of intrinsic light controllers, said controllers changing the light distribution among the sensors to achieve a desired distribution wherein the light controllers focus the light such that the spread of light to detectors is reduced.

41 Claims, 6 Drawing Sheets

LIGHT OUTPUT OPTIMIZATION

RELATED APPLICATION

This application is a continuation of PCT Application number PCT/IL99/00225, filed May 2, 1999, which designates the U.S.

FIELD OF THE INVENTION

The present invention pertains to the field of medical diagnostic imaging and more particularly to the optimization, both quantitatively and qualitatively, of light output from scintillators used in such imaging.

BACKGROUND OF THE INVENTION

Many medical imaging devices such as gamma cameras use a scintillation crystal to detect the radiation that is processed to provide images of the interior of patients. Radiation, such as gamma radiation, that has passed through or out of a patient being imaged impacts the scintillator generating scintillations, i.e. flashes of light. Light sensors such as photomultiplier tubes (PMTs) are optically coupled to the scintillation crystal, generally through transparent means such as a glass plate. The flashes of light which are sometimes referred to as "an event", are detected by the PMTs and converted into electrical pulses. The electrical pulses are processed to provide the images. Thus the scintillation generated light is at the heart of the imaging by devices such as gamma cameras.

In practice, when an event occurs, the light from the scintillation crystal strikes and illuminates an area of the glass coupling the scintillation crystal to the PMTs. The location of the event needed to provide an image is computed with algorithms that use the outputs of the PMTs contiguous to illuminated areas. The accuracy of the location determination, which also effects the image uniformity, is maximized when a plurality of PMTs are illuminated by the event. However, for those portions of the image that are over a single PMT, the events will appear to be bunched at the center of the PMT. For those portions of the image that are between PMTs, light is lost. Both of these effects result in reduced energy and/or position resolution and/or increased noise.

It has been and still is an object of scientists in the field to capture as much of the light as possible and to assure that the light is spread so as to illuminate a plurality of PMTs. However, it is important that the light be distributed in a manner that allows for the determination of the position of the event that caused it.

In many applications in which high energy gamma rays are utilized, the absorbance of the rays by the crystal is poor. To increase the gamma ray capture, a thicker crystal is used. However, such a thicker crystal results in reduced resolution in the image.

When the crystal scintillates, photons of light are transmitted in all directions. Accordingly, much of the light is never sensed by a PMT and is lost. This is exacerbated by the fact that the high refractive index of the crystal results in its acting as a light guide which distributes the light far from the nearby PMTs. To increase the amount of light that is sensed by the PMTs, in the prior art, reflective materials are placed on the surface of the crystal opposite to the surface coupled to the PMTs. The reflective materials capture the light that is emitted in the direction away from the PMTs and transmit it back to the PMTs. In general, this is done by reflection surfaces that are attachments to the crystal. In general, these materials may be specular or diffusive reflectors and are sometimes distributed to improve the distribution of light from events such that better resolution of the positions of the events can be maintained.

Nevertheless, the thickness of scintillator crystals is limited by resolution effects such that much of the radiation in high energy gamma imaging is lost.

U.S. Pat. No. 5,763,887 also shows reflection surfaces that are tailored to cause the light to be reflected towards the PMTs in a manner which improves the event location property of the detector. This patent describes the use of holographic reflectors or light directors that are situated on one or both sides of the crystal. Due to the difficulty in coupling light out of the surface of the crystal, this solution appears to be of limited utility.

It is known from "Performance of a position-sensitive scintillation detector" by J. S. Karp, et al. (Phys. Med. Biol. 1985, Vol. 30, No. 7, pp. 643–655, to provide, in one dimensional detectors, one dimensional surface depressions uniformly spaced on the surface of a scintillation crystal to increase the amount of light transferred to the detectors and to increase the resolution of the detector. However, despite the nearly 14 year that have passed since the publication of this paper, no practical utility in either commercial detectors or in two dimensional detectors has been made.

BRIEF DESCRIPTION OF THE INVENTION

To overcome the faults of the light directing plates that are presently being used, one aspect of some preferred embodiments of the present invention comprises operating on the scintillation crystal per se to intrinsically provide the light direction control desired, using combinations of reflection, refraction, diffraction, or transparency. As used herein, the term "intrinsic" when applied to a scintillator of to functions of a scintillator, means that at least part of the function or structure referred to is part of the body or surface of the scintillator and not completely external to the outer surface of the scintillator.

Thus, some preferred embodiments of the invention provide scintillator crystals that includes intrinsic light direction controllers for optimizing the light output of the scintillator quantitatively and qualitatively. More particularly the light direction controllers include directive reflection surfaces, such as grooves, on the surfaces of the scintillation crystal, pyramids integral to the surfaces of the crystals, cones intrinsic to the surface of the crystals, or crystal surfaces for providing reflection from the crystal surfaces. The crystal surfaces are preferably shaped for directing the light by machining, etching, embossing or forging the surfaces of the crystal.

Thus, this aspect of the invention contemplates modifying the scintillation crystal itself so that it provides the desired light direction control. To this end the surfaces of the crystals are tailored so that the light illuminated areas of the detector are not directly beneath a PMT. The area directly under the PMTs is tailored to reflect light or to diffuse the light so that a greater portion of it strikes the surrounding PMTs rather than being captured for the most part by a single PMT. Thus in general the crystal is modified so that it directs the light towards the side of crystal facing the PMT and in addition directs the light to a group of PMTs rather than to single PMTs.

Furthermore, to avoid loss of light between PMTs, in some preferred embodiments of the invention, the surface of the crystal is formed to redistribute light which would have been lost between the PMTs so that the light is captured by a group of PMTs.

There are certain cases where it is desired to isolate the light so that its spread is reduced, so that it strikes only a small group of PMTs. The invention contemplates modifying the scintillator crystal in the manner which will also accomplish this isolation of the emitted light. For example, when a thick crystal is used focusing can reduce the light spread such that the spread is reduced to that of a scintillator half as thick. This allows for the use of thicker scintillator crystals (with higher capture efficiency) with the resolution of thinner crystals.

The direction of the light is controlled by machining such as by engraving or by pressing, or by embossing or even by etching the crystal to have a multiplicity of intrinsic small pyramids or rings or other forms on the surfaces thereof to direct the light as desired. Thus, for example, the pyramids can be located in defined areas and absent from other defined areas or replaced by grooves or cones in other defined areas. Thus, the pyramids can be located in a checkerboard type configuration wherein certain sections of the surfaces of the crystal have pyramids thereon other sections have simple diffraction or reflection type surfaces, and still other surfaces enable light to pass directly therethrough.

There is thus provided, in accordance with a preferred embodiment of the invention, a scintillator, having two faces, for use in medical diagnostic imaging devices, said devices including a plurality of light sensors for converting light generated in said scintillators to electrical signals, processors for converting the electrical signals to images and a monitor for displaying the images, said scintillator including a two dimensional distribution of intrinsic light controllers, said controllers changing the light distribution among the sensors to achieve a desired distribution.

Preferably, the light controllers focus the light such that the spread of light to detectors is reduced.

Preferably, the light controllers redirect light that would strike a sensor in their absence to a farther sensor.

Preferably, the light controllers increase the light directed to the sensors.

In a preferred embodiment of the invention, the density of light controllers varies with their position on the scintillator.

In a preferred embodiment of the invention, the scintillator has a bottom face optically coupled to said light sensors and a top face spaced apart from said bottom face, and the light controllers include a plurality of angled surfaces in at least one of the faces of the scintillator for directing light that strikes the planar surfaces.

Preferably, the angled surfaces form depressions in the face. Alternatively or additionally, the angled surfaces form elevations in the face. In a preferred embodiment of the invention, the depressions and/or elevations, intersect.

In a preferred embodiment of the invention, the angled surfaces form pyramids, which direct the light impinging thereon to the sensors. In a preferred embodiment of the invention, the angles of the pyramids vary according to their position on the surface of the scintillator.

In a preferred embodiment of the invention, the angled surfaces are planar surfaces.

In a preferred embodiment of the invention, the angled surfaces form cones in the surface of the scintillator.

In a preferred embodiment of the invention, the angled surfaces form grooves.

In a preferred embodiment of the invention, at least some of the controllers are coated with reflective coating. In a preferred embodiment of the invention, the reflective coating includes tiny glass balls.

In a preferred embodiment of the invention, the controllers are formed in the face of the scintillator facing the sensors. In a preferred embodiment of the invention, the controllers are formed in the face of the scintillator facing away from the sensors.

In a preferred embodiment of the invention, the light controllers are arranged in a checkerboard fashion.

In a preferred embodiment of the invention, the intrinsic light controllers are formed directly above the sensors in the surface of the scintillator facing the sensors. Alternatively or additionally, the intrinsic light controllers are formed in a surface of the scintillator directly above regions at which no sensor is placed.

in a preferred embodiment of the invention, wherein the scintillator has dispersed therein material for absorbing scintillations.

There is further provided, in accordance with a preferred embodiment of the invention, a scintillator, having two faces, for use in medical diagnostic imaging devices, said devices including a plurality of light sensors for converting light generated in said scintillators to electrical signals, processors for converting the electrical signals to images and a monitor for displaying the images, said scintillator having dispersed therein material for absorbing light produced by scintillations Preferably, the scintillator has dispersed therein scatter material to scatter the scintillations.

Preferably, the edges of the scintillator are biased to reduce spread of light to sensors far from the edge.

In a preferred embodiment of the invention, the material is a colorant.

There is farther provided, in accordance with a preferred embodiment of the invention, a scintillator, having two faces, for use in medical diagnostic imaging devices, said devices including a plurality of light sensors for converting light generated in said scintillators to electrical signals, processors for converting the electrical signals to images and a monitor for displaying the images, said scintillator having a dispersed therein material which scatters light produced by scintillations.

Preferably, the edges of the scintillator are biased to reduce spread of light to sensors far from the edge.

There is further provided, in accordance with a preferred embodiment of the invention, a scintillator, having two faces, for use in medical diagnostic imaging devices, said devices including a plurality of light sensors for converting light generated in said scintillators to electrical signals, processors for converting the electrical signals to images and a monitor for displaying the images, wherein the edges of the scintillator are biased to reduce spread of light to sensors far from the edge.

In a preferred embodiment of the invention, the scintillator includes shaped light guides which guide light from the scintillator to the sensors, the total area of the sensors being smaller than the total area of the scintillator.

There is further provided, in accordance with a preferred embodiment of the invention, a scintillator, having two faces, for use in medical diagnostic imaging devices, said devices including a plurality of light sensors for converting light generated in said scintillators to electrical signals, processors for converting the electrical signals to images and a monitor for displaying the images, and including shaped light guides which guide light from the scintillator to the sensors, the total area of the sensors being smaller than the total area of the scintillator.

Preferably, the light guides have the general shape of a truncated cone or pyramid. Preferably, the surfaces of the light guides are coated with a light reflecting material.

There are further provided, methods of forming a scintillator crystal in accordance with a preferred embodiment of the invention by machining the surface, etching the surface embossing the surface or of forging the light guids in the surface.

BRIEF DESCRIPTION OF THE DRAWINGS

The present invention is illustrated by way of example but not by way of limitation in the figures of the accompanying drawings of which like reference numbers indicate similar elements; and in which.

DETAILED DESCRIPTION OF PREFERRED EMBODIMENTS

The present invention is concerned with scintillators used, for example, in gamma cameras and more particularly with the optimization of the light emitted by the scintillator crystal responsive to gamma radiation striking the scintillator. Generally, Gamma camera scintillators are large NaI crystals doped with Thallium. Unfortunately, the scintillation crystals produce flashes of light which are not only transmitted toward the light sensors but are transmitted in all directions in the scintillator. The light that reaches the bottom of the scintillator goes through a coupling layer (usually glass) and is applied to light sensors such as photomultiplier tubes, for example. The PMTs convert the light of each event into electrical pulses. The electronics of the gamma camera converts the light pulses to image data. A pulse height analyzer or similar circuitry is used to differentiate a natural event from a scatter caused event. Gating based on the response of the pulse height analyzer enables the display of events on the display monitor in the form of an image.

Figure 1:
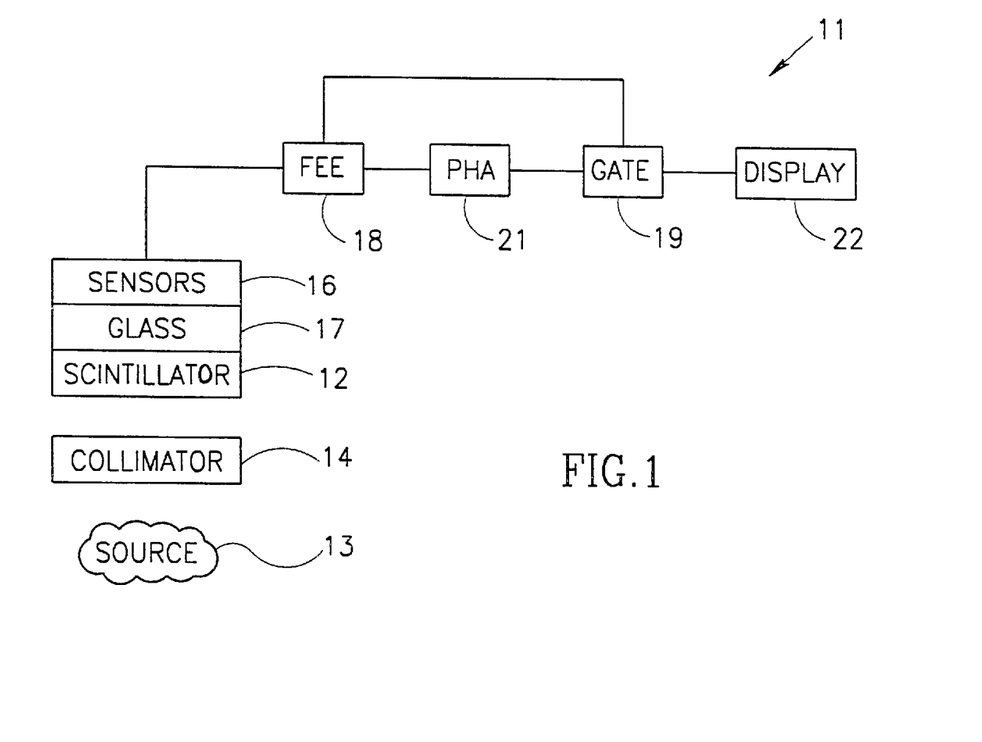
FIG. 1 is a generalized and simplified block diagram of a typical gamma camera imaging system.

As shown in FIG. 1, a gamma camera device 11 comprises a scintillator 12 that receives radiation from a source 13 such as a patient who has ingested radioisotopes. The radiation proceeds via a collimator 14 to the scintillator. The radiation causes scintillations, i.e., flashes of light in the scintillator. The light sensors, such as PMTs, shown as block 16, detect the flashes of light. The PMTs are coupled to the scintillator through a glass plate 17. The electrical signals from the sensors are fed to the front end electronics (FEE) 18. The output of the front end electronics is a signal that is a function of the position of the "event" in the patient, i.e., inchoate image data. Before it can be used as image data it must pass through a gate 19. Gate 19 operates, i.e., opens or closes, responsive to the output of a pulse height analyzer 21 to provide image signals. The pulse height analyzer is designed to weed out scatter caused pseudo-events. Thus the output of gate 19 are image signals which cause the event to appear on a display monitor shown at 22.

The greater the light collection efficiency of the scintillator the better, since, energy resolution is a function of the quantity of light. In addition, the spatial resolution is a function of the light output; the slope of the light fallout curve and the light spread. Thus the energy resolution is limited by the light output as is the spatial resolution. The uniformity of the image is dependent on the location of the areas of the glass plate 17 that are illuminated vis-a-vis the PMTs. The dependence of position and energy resolution and image uniformity on the light distribution is very well known in the art.

In accordance with a preferred embodiment of the invention, light output direction is controlled to optimize the quantity of capture and quality of distribution of the light. The quantity of the light as used herein is the actual amount of light that is collected per scintillation. The quality of the light as used herein is determined by the areas of plate 17 that are illuminated in relation to the location of the PMTs as compared to an ideal distribution.

Figure 2:
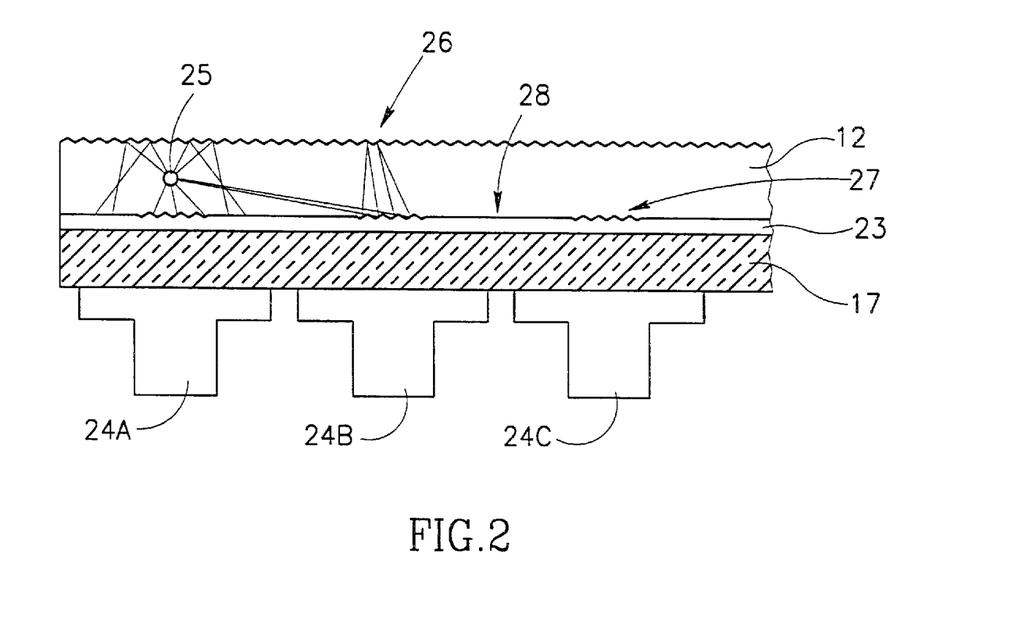
FIG. 2 illustrates a scintillator, glass plate, PMT sandwich, with the scintillator crystal itself intrinsically providing the directional light control, in accordance with a preferred embodiment of the invention.

In accordance with a preferred embodiment of the invention, the crystal itself is intrinsically modified to include intrinsic funnels, grooves, pyramids, and any other intrinsic shapes, on one or both faces, that can be used for controlling the direction of the light generated by the scintillation in the crystal. Examples of the modification of the scintillation crystal are shown in the accompanying drawings. For example, FIG. 2 shows a scintillating crystal 12 which may be attached by a layer of glue 23 though a plate of glass 17 to a multiplicity of light sensors such as PMTs 24A, 24B, 24C. As is well known there are many more sensors in a typical gamma camera arrangement than are shown in the drawings. Thus FIG. 2 is a cross sectional view of a small portion of the typical detector sandwich used for generating light photons and for converting the light to electrical signals.

What is shown in FIG. 2 that is especially new and unique is the modification of the crystal 12 indicated by grooving 26 at the top of the crystal and/or grooving 27 at the bottom of the crystal. The grooves may be arranged in checker board like sections of reflection causing grooving such as section 27 and non reflective comparatively transparent sections at the bottom of the crystal, such as section 28. Thus, as shown in FIG. 2 the crystal has been modified so that light photons emitted due to an event are reflected from the top surface of the crystal back towards PMTs, near the event. Also the light that would otherwise illuminate merely the bottom of a single photomultiplier tube is reflected back into the crystal and again reflected back towards the PMTs so that it is spread to a plurality of PMTs enhancing the resolution and the event location determination capabilities of the system. For example, the light from event 25 that strikes the top surface of the crystal is shown being reflected back towards the PMTs and the light striking toward the middle of a PMT is shown being spread towards other PMTs. Alternatively, light from the top may be retroreflected such that it is reflected back toward the event. Thus, the effect of the top surface of the scintillator is nullified. To reduce the effects of thickness on resolution, the upper surface may provide focusing of the light which hits it. Further, the focusing effect may vary depending on the distance from the PMT axis, to optimize the distribution of the light.

Grooves 27 may be used to redirect light, which is directed toward the center of a PMT, toward other PMTs. Additionally or alternatively, grooves may be provided between the PMTs to redirect light directed toward these areas (which would normally be lost), back into the scintillator and thus to the adjoining PMTs.

It will be understood that many distributions of light may be achieved based on different distributions and types of grooving on both the top and bottom surfaces of the scintillator.

Figure 3A:
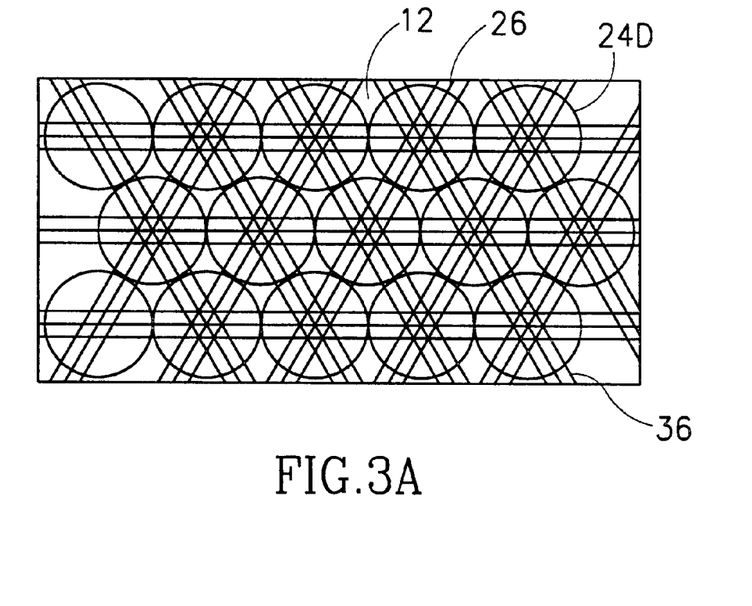
FIG. 3A shows one type of grooving used to provide the light direction control, in accordance with a preferred embodiment of the invention.
Figure 3B:
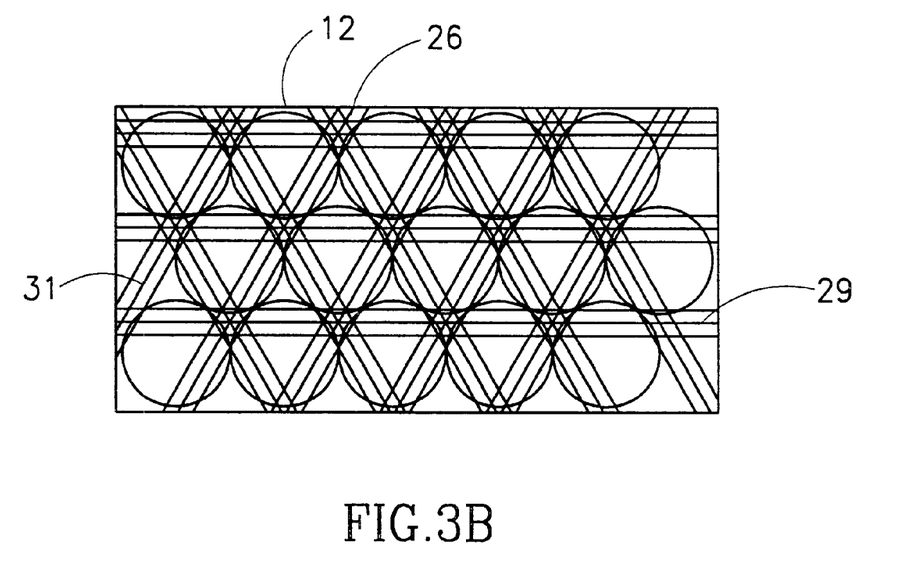
FIG. 3B shows a modified grooving method similar to that of FIG. 3A but having different light beam direction results, in accordance with a preferred embodiment of the invention.

FIGS. 3A and 3B schematically show examples of multiple hexagonal grooving that may be used for modifying the surface of crystal. More particularly, FIG. 3A shows multiple grooves that intersect over the PMTs. In FIG. 3A, scintillator crystal 12 is shown as having the PMTs such as PMT 24D positioned so that the grooves such as grooves 26, 29 and 31 intersect over the PMTs. Thus, the PMT will be preferentially optically coupled to the intersection of the grooves. Alternatively, grooving may be provided only directly over the PMTs.

FIG. 3B on the other hand shows the crystal 12 machined or etched so that the grooves, such as grooves 26, 29 and 31 intersect between the PMTs. Variations of the points of intersection of the grooves can of course be done in order to provide reflection or more generally to control the direction of the light as desired or required.

In other preferred embodiments of the invention, where etching or embossing is used to form the pyramids, the pyramids may be provided only in regions in which they are desired without machining lines in regions in which they are not required. Furthermore, the angle of the grooves may be varies as required, with 72 degrees being used for retroreflection, a larger angle for some spreading and a smaller angle for focusing. In particular, densely packed pyramids, backed with reflecting material, may be provided on the PMT side of the crystal over the areas near the intersections between PMTs. Directly opposite the intersections, the angle may be increased to spread the light to adjoining PMTs. At the center of the PMTs, a diffusing surface (or a low density of pyramid's) may be provided on the PMT side of the crystal, to reduce the light to the center of the PMT. (Of course, no reflecting material is provided between the crystal and the PMTs. The pyramids at the opposite surface of the crystal may be made somewhat spreading and/or the pyramids may be spaced. (as indicated below in FIG. 4B).

Figure 3C:
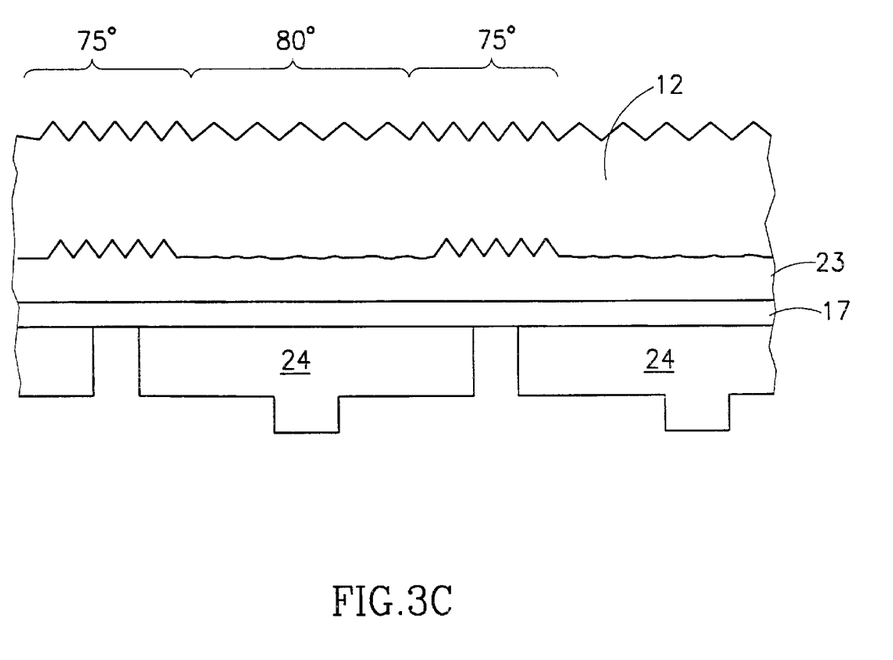
FIG. 3C shows a preferred layout of pyramids in the surfaces of the crystal.

FIG. 3C shows a possible layout of pyramids on a crystal, in accordance with a preferred embodiment of the invention. In this embodiment, a combination of reflector coated 72 degree pyramids at the intersection of the PMTs and 75–80 degree angle pyramids on the opposite side of the crystal assure complete collection of the light from events at the intersections without excessive spreading. The diffuse surface at the PMT centers coupled with the pyramids on the other side of the crystal results in a reduction of hot spots without substantial reduction in resolution. Overall, the pyramids on the outside of the crystal result in a large increase in resolution, especially important when thick detector crystals are used.

Figure 4A:
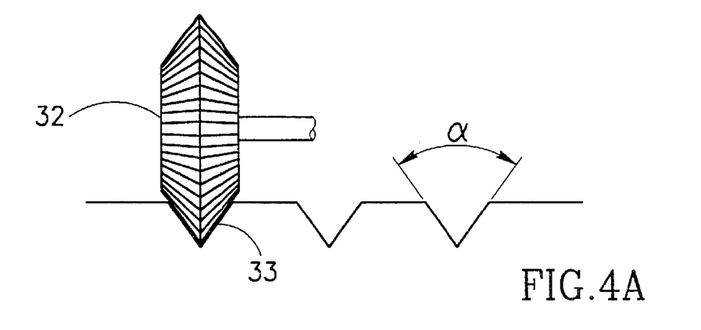
FIGS. 4A–4C illustrate typical tools for producing grooves and grooving in a crystal, in accordance with preferred embodiments of the invention.
Figure 4B:
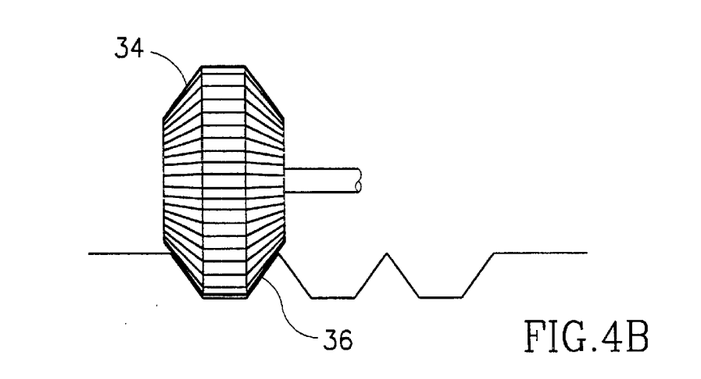

FIGS. 4A and 4B show examples of the type of tools that can be used for engraving the grooves and provides cross-sectional views of exemplary grooves. More particularly, FIG. 4A shows a pointed engraving tool 32 causing a pointed groove 33 that has sides at an angle $\alpha$. In a preferred embodiment the angle $\alpha$ is equal to 72 degrees or some other angle as described above; however, in many cases larger or smaller angles would be used.

Figure 4C:
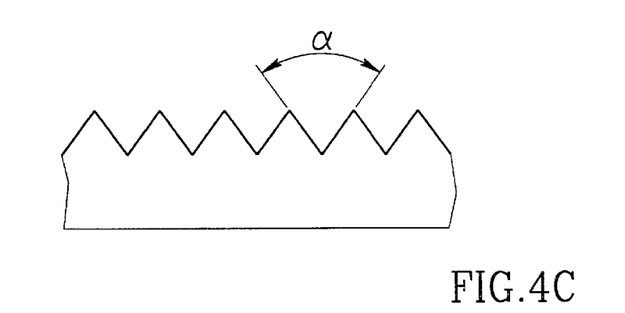

FIG. 4B shows a modification of the tool and the groove of FIG. 4A. More particularly the tool 34 in FIG. 4B produces a groove with sloping sides and a flat bottom, as distinguished from the groove of FIG. 4A. Thus the groove 36 of FIG. 4B has sloping sides which slope also an angle $\alpha$ but that has a flat bottom. FIG. 4C shows grooves sloping at an angle and with no spacing between the grooves. This is in contrast to the grooves of FIG. 4A where there is spacing between the grooves. While a change in angle affects the angle of spread of the light falling into the grooves, a reduction in the density of crystals effects the percentage of light from an event that is effected by the pyramids.

Figure 4D:
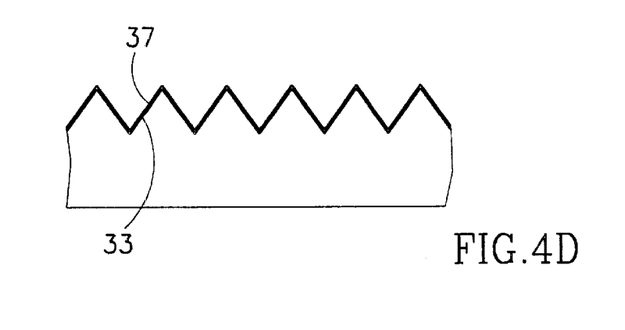
FIG. 4D shows the surface of a scintillator crystal provided with grooves and a reflective coating, in accordance with a preferred embodiment of the invention.

A modification that is applied to any of the grooves that are made in the crystal is shown in FIG. 4D. More particularly FIG. 4D shows, as an example, grooves such as groove 33 having a reflective coating 37 applied thereto. The reflective coating can be aluminum or silver plate or any other reflective coating. A particularly suitable reflective coating may be a paint containing small glass balls which operate to diffract the light. Such paint is commercially available from 3M Company. It should be noted that due to its high index of refraction, the surface of the scintillator crystal is naturally partly reflective.

Figure 5:
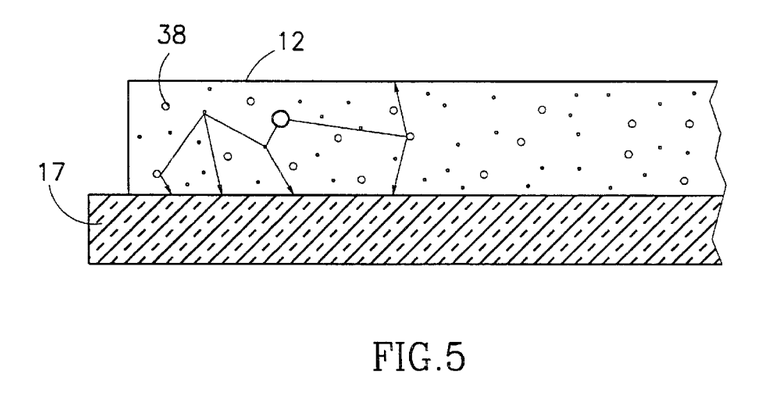
FIG. 5 schematically illustrates a scintillator crystal modified by implanting scatter material therein, in accordance with a preferred embodiment of the invention.

FIG. 5 shows another modification of the crystal, in accordance with some preferred embodiments of the invention. This modification can be combined with the modifications already described or can be used by itself. In this modification scatter material 38 is added to the crystal when the crystal is formed. The scatter material may be, for example, air bubbles, impurities, colloidal suspensions or sintered powder material. Alternatively, the crystal may be made slightly attenuating by coloration or by the addition of absorbing materials.

In FIG. 5 the scatter material is indicated by little dots, such as little dot 38. The scatter material within the crystal tends to cause light scintillations to be scattered so that the light is not concentrated under a single PMT but instead is spread naturally and normally under a multiplicity of PMTs. Also the scatter material (or absorption) may be used to assure that the spread of the light is curtailed. As indicated above, excess light spread reduces the system's linearity and resolution.

Figure 6A:
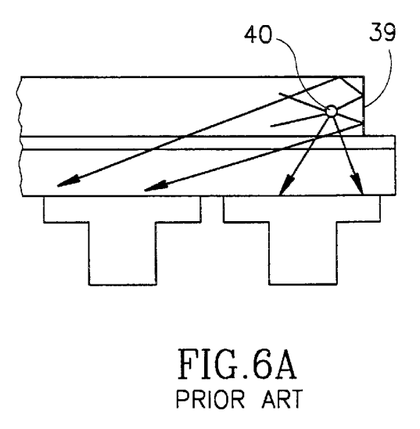
FIG. 6A illustrates a crystal having an orthogonal edge as generally provided in the art.
Figure 6B:
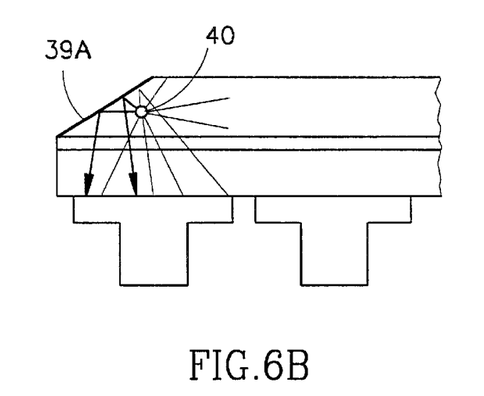
FIG. 6B shows a crystal modified by having at least one biased edge to increase the field of view provided by the PMTs, in accordance with a preferred embodiment of the invention.

FIGS. 6A and 6B show additional crystal modifications, in accordance with a preferred embodiment of the invention. The modification to the crystal of FIGS. 6A and 6B is illustrated particularly by differences in FIG. 6B as compared to FIG. 6A. It is well known that the edges of the crystal are particularly notorious for poor light direction characteristics. More particularly as shown in FIG. 6A (which illustrates the normal edge of crystals) crystal 12 typically has a side 39 that is perpendicular to the top and bottom sides of the crystal. The light from the scintillations in such crystals which reach the side wall are generally reflected by the wall. However, they do not reach the nearby PMTs. An event 40 is shown as having much of its light reflected by edge 39 in this manner. It should be noted that the modification of FIG. 6 may be used with or without the other modification of the invention.

FIG. 6B shows a biased side wall 39A which reflects light to nearby PMTs. Sidewall 39A may be formed in the crystal itself or may be formed in separate glass or crystal pieces attached to a square edged crystal, to reduce the cost of manufacture. In this configuration preferably only the biased (beveled) portion is made of glass, forming a section having a triangular cross-section abutting the square edge of the crystal.

Figure 7:
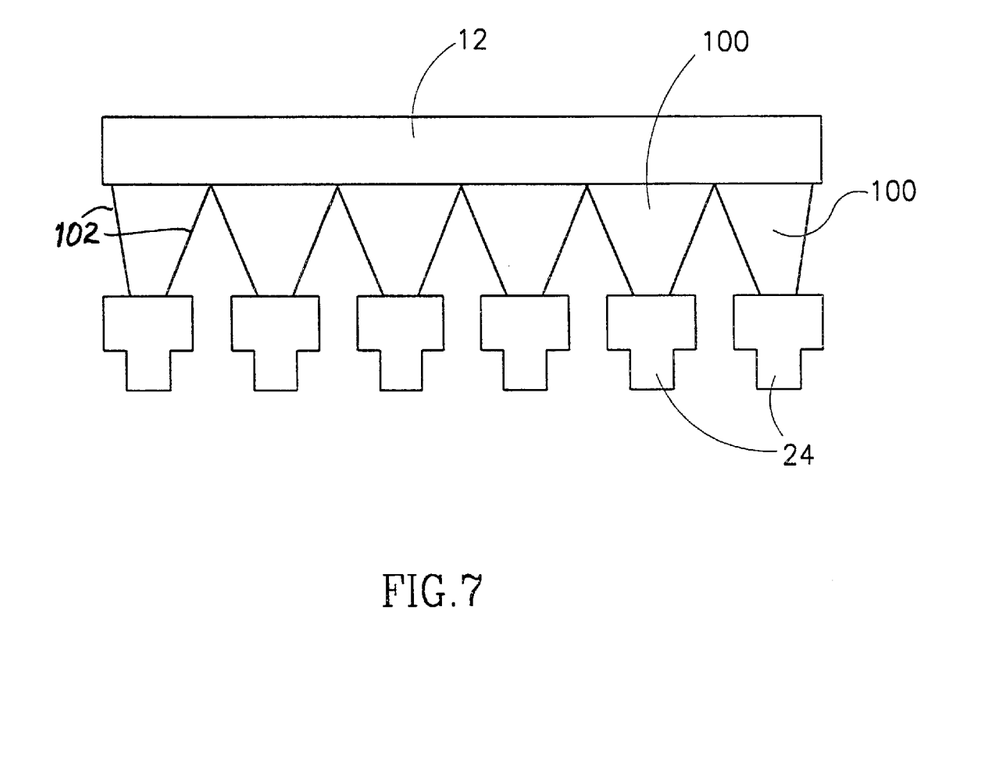
FIG. 7 shows a method of light funneling for reducing the light loss from events occurring at the of or between sensors.

FIG. 7 shows another method of reducing the losses of light from events occurring at the intersections of PMTs. In this preferred embodiment of the invention, the light from the crystal is funneled by light funnels 100 from crystal 12 to PMTs 24. Funnels 100 preferably have a hexagonal shape at the crystal side, so that the entire surface is covered and have a circular face at the PMT to match the PMT active area. Preferably, walls 102 of pyramids 100 are coated with reflecting material. It should also be understood that the use of funnels allos for complete coverage of the face of the crystal while using only one size of sensor. In the past, a smaller size sensor has been used for at least some of the sensors at the edge of the scintillator.

The above embodiments each include a number of features. It should be understood that various combinations of features from the various embodiments are also possible as are embodiments that do not have all of the features of any particular embodiment. Furthermore, while pyramidal structures are described, the pyramids may be rectangular or hexagonal pyramids or they may be replaced by cones.

While the present invention is described using particular embodiments, it should be appreciated that the invention should not be construed as limited by such embodiments but rather construed according to appended claims. As used herein, the terms "comprise" and "include" and their conjugates mean "including but not limited to."

What is claimed is:

1. A scintillator, having two faces, for use in medical diagnostic imaging devices, said devices including a plurality of light sensors for converting light generated in said scintillator to electrical signals, processors for converting the electrical signals to images and a monitor for displaying the images, said scintillator including a two dimensional distribution of intrinsic light controllers, said controllers changing the light distribution among the sensors to achieve a desired distribution, wherein characteristics of the light controllers varies with their position on the scintillator and wherein said light controllers are present on or in both faces of the scintillator.

2. A scintillator according to claim 1 wherein the characteristics comprise the density of the controllers.

3. A scintillator according to claim 1, wherein said scintillator have a bottom face optically coupled to said light sensors and a top face spaced apart from said bottom face, wherein said light controllers include a plurality of angled surfaces in both faces of the scintillator for directing light that strikes the faces, wherein the angled surfaces form pyramids, which direct the light impinging thereon to the sensors, which angles vary according to their position on the face of the scintillator.

4. A scintillator, having two faces, for use in medical diagnostic imaging devices, said devices incuding a plurality of light sensors for converting light generated in said scintillator to electrical signals, processors for converting the electrical signals to images and a monitor for displaying the images, said scintillator including a two dimensional distribution of intrinsic light controllers on or in said faces, said controllers changing the light controllers changing the light distribution among the sensors to achieve a desired distribution, wherein characteristics of the light controllers varies with their position on the scintillator and wherein said light controllers are present on or in at least one of said faces at positions that are not directly under an active area of a sensor of said plurality of sensors.

5. A scintillator according to claim 4 wherein the characteristics that vary comprise the density of the controllers.

6. A scintillator according to claim 4 wherein the characteristics that vary comprise a reflection angle of the controllers.

7. A scintillator according to claim 6, wherein said scintillator have a bottom face optically coupled to said light sensors and a top face spaced apart from said bottom face, wherein said light controllers include a plurality of angled surfaces in at least one of the faces of the scintillator for directing light that strikes the angled surfaces, wherein the angle surfaces form pyramids, which direct the light impinging thereon to the sensors, which angles vary according to their position on the surface of the scintillator.

8. A scintillator according to claim 4 wherein the light controllers form cones in the surface of the scintillator.

9. A scintillator according to claim 4 wherein the controllers comprise angled surfaces forming grooves.

10. A scintillator, having two faces, for use in medical diagnostic imaging devices, said devices including a plurality of light sensors for converting light generated in said scintillator to electrical signals, processors for converting the electrical signals to images and a monitor for displaying the images, said scintillator having dispersed therein material for absorbing light produced by scintillations.

11. A scintillator according to claim 10 wherein the material is a colorant.

12. A scintillator according to any of claims 1–3 or 10, wherein the scintillator has dispersed therein scatter material to scatter the scintillations.

13. A scintillator according to any of claims 1, 10, 2 or 3 wherein the edges of the scintillator are biased to reduce spread of light to sensors far from the edge.

14. A scintillator according to any of claims 1, 10, 2 or 3 and including shaped light guides which guide light from the scintillator to the sensors, the total area of the sensors being smaller than the total area of the scintillator.

15. A scintillator according to claim 2 or claim 3, wherein the scintillator has dispersed therein material for absorbing scintillations.

16. A scintillator according to any of claims 1, 2 or 3 wherein at least some of the light controllers focus the light such that the spread of light to sensors is reduced.

17. A scintillator according to any of claims 1, 2 or 3 wherein at least some of light controllers redirect light that would strike a sensor in their absence to a farther sensor.

18. A scintillator according to any of claims 1, 2 or 3 wherein at least some of the light controllers increase the light directed to the sensors.

19. A gamma camera according to claim 1 or claim 4 wherin the characteristics of the intrinsic light controllers on both faces vary with position.

20. A scintillator, according to any of claims 4, 5 or 7 wherein the controllers are formed in the face of the scintillator facing the sensors.

21. A scintillator, according to any of claims 4–9 wherein the controllers are formed in the face of the scintillator facing away from the sensors.

22. A scintillator, according to any of claims 4–9 wherein the controllers are formed in both faces of the scintillator.

23. A scintillator according to any of claims 4, 5 or 7, wherein the scintillator has dispersed therein material for absorbing scintillations.

24. A scintillator according to any of claims 4, 5 or 7, wherein the scintillator has dispersed therein scatter material to scatter the scintillations.

25. A scintillator according to any of claims 4, 5 or 7 wherein the edges of the scintillator are biased to reduce spread of light to sensors far from the edge.

26. A scintillator according to any of claims 4, 5 or 7 and including shaped light guides which guide light from the scintillator to the sensors, the total area of the sensors being smaller than the total area of the scintillator.

27. A scintillator according to any of claims 4–9 wherein at least some of the light controllers focus the light such that the spread of light to sensors is reduced.

28. A scintillator according to any of claims 4–9 wherein at least some of light controllers redirect light that would strike a sensor in their absence to a farther sensor.

29. A scintillator according to any of claims 4–9 wherein at least some of the light controllers increase the light directed to the sensors.

30. A scintillator, having two faces, for use in medical diagnostic imaging devices, said devices including a plurality of light sensors for converting light generated in said scintillator to electrical signals, processors for converting the electrical signals to images and a monitor for displaying the images, said scintillator including a two dimensional distribution of intrinsic light controllers, said controllers changing the light distribution among the sensors to achieve a desired distribution, wherein at least some of the controllers are coated with reflective coating including tiny glass balls.

31. A scintillator according to claim 30 wherein the controllers are formed in or on at least one of the faces.

32. A scintillator, having two faces, for use in medical diagnostic imaging devices, said devices including a plurality of light sensors for converting light generated in said scintillator to electrical signals, processors for converting the electrical signals to images and a monitor for displaying the images, said scintillator including a two dimensional distribution of intrinsic light controllers, said controllers changing the light distribution among the sensors to achieve a desired distribution, wherein characteristics of the light controllers varies with their position on the scintillator and wherein said light controllers are present on or in both faces of the scintillator, wherein the characteristics comprise a reflection angle of the controllers.

33. A scintillator according to claim 32 wherein at least some of the light controllers focus the light such that the spread of light to sensors is reduced.

34. A scintillator according to claim 32 wherein at least some of light controllers redirect light that would strike a sensor in their absence to a farther sensor.

35. A scintillator according to claim 32 wherein at least some of the light controllers increase the light directed to the sensors.

36. A gamma camera, for use in medical diagnostic imaging comprising:

a scintillator having two faces and including a two dimensional distribution of intrinsic light controllers on or in said faces, said controllers changing the light distribution among the sensors to achieve a desired distribution, wherein characteristics of the light controllers varies with their position on the scintillator;

a plurality of light sensors for converting light generated in said scintillator to electrical signals;

processors for converting the electrical signals to images; and a monitor for displaying the images.

37. A gamma camera, for use in medical diagnostic imaging comprising:

a scintillator having first and second faces;

a plurality of light sensors situated to view said first face and operative to convert light generated in said scintillator to electrical signals;

processors for converting the electrical signals to images; and a monitor for displaying the images, the scintillator including a two dimensional distribution of intrinsic light controllers on or in at least said second face, said controllers changing the light distribution among the sensors to achieve a desired distribution, wherein characteristics of the light controllers on said second face varies with their position on the scintillator.

38. A gamma camera according to claim 37 including a two dimensional distribution of intrinsic light controllers on or in said first face.

39. A gamma camera according to claim 38 wherein characteristics of said light controllers on said first face varies with their position on the scintillator.

40. A gamma camera according to any of claims 37–39 wherein the characteristics that vary comprise the density of the controllers.

41. A gamma camera according to any of claims 37–39 wherein the characteristics that vary comprise a reflection angle of the controllers.

* * * * *